US007323600B1

(12) United States Patent
Turoff et al.

(10) Patent No.: US 7,323,600 B1
(45) Date of Patent: Jan. 29, 2008

(54) PROCESS FOR IMPROVING THE CONVERSION OF OXAZOLIDONES TO ALKANOLAMINES

(75) Inventors: Michael L. H. Turoff, League City, TX (US); Arthur Lee Cummings, League City, TX (US); Scott William Waite, Reno, NV (US); Robert Lee Horan, Houston, TX (US)

(73) Assignee: MPR Services, Inc., Dickinson, TX (US)

( * ) Notice: Subject to any disclaimer, the term of this patent is extended or adjusted under 35 U.S.C. 154(b) by 0 days.

(21) Appl. No.: 11/463,182

(22) Filed: Aug. 8, 2006

(51) Int. Cl.
*C07C 209/84* (2006.01)
*C07C 209/86* (2006.01)
(52) U.S. Cl. .................... 564/497; 564/475; 564/477
(58) Field of Classification Search ................ 564/497
See application file for complete search history.

(56) References Cited

U.S. PATENT DOCUMENTS 4,138,468 A * 2/1979 Kettner et al. .............. 423/228

* cited by examiner

Primary Examiner—Brian Davis
(74) Attorney, Agent, or Firm—Alston & Bird LLP

(57) ABSTRACT

There is provided a regeneration process for converting oxazolidones such as hydroxypropyloxazolidone (HPOZD) to alkanolamines such as di-isopropanolamine (DIPA) and $CO_2$. An amine stream containing HPOZD joins a stream that includes a caustic solution. The combined stream is passed to a tank where the caustic reacts with HPOZD to convert it to DIPA and $CO_2$. The conversion of HPOZD to DIPA and $CO_2$ requires a ratio of at least 2 moles of hydroxide for each mole of HPOZD in the solution. The conversion reaction is carried out in a reaction vessel at a temperature above 60° C. The reaction mixture is held in a feed tank for approximately 2 hours while being constantly mixed. After the reaction is completed, the mixture is allowed to settle which results in the virtually complete separation of the amine phase (containing DIPA, and water) from the caustic phase. After an appropriate settling interval, a portion of the caustic phase is drawn from the reaction mixture as a waste/neutralization stream while the other portion of the caustic phase and a very small portion of the amine phase may be sent to a recycle tank for use in subsequent reaction steps. The majority of the amine phase is treated using ion exchange resins to remove excess cations from the amine and clean amine is returned to the amine system.

12 Claims, 1 Drawing Sheet

PROCESS FOR IMPROVING THE CONVERSION OF OXAZOLIDONES TO ALKANOLAMINES

BACKGROUND OF THE INVENTION

1. Field of the Invention

The present invention provides a process for recovering alkanolamines. More specifically, the present invention is an improved process for converting an oxazolidone such as hydroxypropyloxazolidone (HPOZD; [3-(2-hydroxypropyl)-5-methyl-2-oxazolidinone]) to di-isopropanolamine (DIPA).

2. Description of Related Art

In the processing of gas and liquid streams, acid gas impurities (typically hydrogen sulfide and carbon dioxide) are removed by contact with an alkanolamine solution containing an alkanolamines such as DIPA. Alkanolamine solutions are used because of their relatively high absorption capacity of acid gases, and the relative ease with which acid gases can be stripped from the amine-containing solution.

One such process yields HPOZD, an impurity reaction product of the DIPA and carbon dioxide ($CO_2$). The reaction forming the HPOZD molecule occurs with the simultaneous dehydration of one water molecule ($H_2O$) from the DIPA molecule. Other such processes yield analogous oxazolidones using other alkanolamines.

An existing process for converting this impurity (the HPOZD) requires several lengthy stepwise heating and processing cycles at dilute caustic (with corresponding cation) concentrations. This process is tailored to convert the oxazolidone back to DIPA, releasing $CO_2$ into the amine solution to form carbonates and/or bicarbonates, subsequently removing the majority of the cations from the entire reaction solution using ion exchange resins. Because of the concern of the capacity to remove cations from the reaction solution, the concentration of the caustic reactant is kept low, resulting in a process that has a typical HPOZD to DIPA conversion efficiency of about 20% to 25% per reaction process step. The entire reaction mixture including all cations from the added caustic is processed through the ion exchange resins. The overall process including rinsing and regenerating the cation exchange resins adds considerable amounts of water to the amine-containing solution which must be removed by a distillation procedure.

This existing process treats a quantity of an amine-containing solution obtained from an acid gas stripper column used for acid gas removal. The amine-containing solution may be composed of an alkanolamine such as DIPA, a physical solvent such as tetramethylene sulfone, water, $CO_2$ and the degradation product identified as HPOZD. This solution is treated with a dilute caustic solution, such as but not limited to potassium hydroxide (KOH), at elevated temperatures at atmospheric pressure to hydrolyze (add one molecule of $H_2O$) to the HPOZD molecule and simultaneously cleave the $CO_2$ molecule out of the HPOZD molecule, resulting in the production of free DIPA as well as carbonates and/or bicarbonates. The DIPA generated by this process is a benefit to the user in that it is a primary active ingredient of the amine-containing solution used for acid gas removal. The reduction of the HPOZD content of the amine-containing solution used for acid gas removal by this process is a benefit in that the HPOZD decreases the efficiency of the amine-containing solution to perform its function of scrubbing acid gas from gas and/or liquid process streams.

After processing the amine solution through the cation exchange resins, it is returned as "clean amine" to the amine circulation system where excess water and $CO_2$ (from carbonates and/or bicarbonates) are stripped from the solution.

BRIEF SUMMARY OF THE INVENTION

It is therefore the general object of the present invention to provide a more efficient process for treating an amine-containing solution that contains the HPOZD impurity, converting the solution to a "clean amine" solution that can be returned to the customer for reuse.

There is provided a reaction process for converting HPOZD to DIPA and $CO_2$. A rich (acid gas laden) amine stream is introduced into an amine regenerator/stripper column. Steam is generated by boiling the amine solution in the regenerator reboiler. The steam generated from the reboiled amine is introduced near the bottom of the amine stripper and passes upward through the amine solution and the stripping vapor sweeps the acid gases away from the amine solution and out of the top of the stripper. The acid gasses are thereby stripped from the amine solution, producing a "lean amine" solution. The hot lean amine stream exits the bottom of amine stripper and is routed back to the absorber where it absorbs additional acid gasses, becoming "rich" again, and recirculates back to the regenerator/stripper column where it is once again made "lean." Over the course of time, HPOZD is accumulated in the amine solution due to a side reaction of $CO_2$ with DIPA.

To convert HPOZD back to DIPA, a portion of the lean amine containing the HPOZD impurity is transferred into a reaction container (feed tank) where it is mixed with a solution that includes a caustic solution (typically but not limited to KOH) from either a caustic supply vessel and/or a "recycle caustic" tank. The combined streams are then aggressively mixed at prescribed temperatures (see below) in the feed tank where the caustic reacts with HPOZD to convert it to DIPA and $CO_2$.

The conversion of HPOZD to DIPA and $CO_2$ stoichiometrically requires two moles of hydroxide ($OH^-$) for each mole of HPOZD present in the solution to ensure a reasonably complete conversion of the HPOZD. However, it has been found that using that exact ratio does not provide sufficient driving force to cause the reaction to go to completion. Achieving complete conversion of the HPOZD back to DIPA requires a ratio of at least 2.0 but preferably more than 2.2 moles of hydroxide for each mole of HPOZD in the solution and one mole of hydroxide for each mole of "bound amine" (a protonated amine=an $H^+$ bound to the amine) present in the solution. More specifically, to have some residual recoverable caustic value in the caustic phase of the reaction mixture, a ratio of 2.5 moles of hydroxide for each mole of HPOZD present and at least one mole of hydroxide for each mole of "bound amine" present in the solution is desirable. (Note: A hydroxide molecule reacts with a bound amine molecule to free the amine molecule and yield one $H_2O$ molecule.)

The conversion reaction is carried out in a reaction vessel at a temperature above 60° C., preferably between 60° C. and 120° C., and most preferably from 80° C. to 100° C. The reaction mixture is held in a feed tank at the reaction temperature for approximately 2 hours while being constantly mixed to maximize the contact between the caustic phase and the lean amine solution. (It has been observed that the concentrated caustic solution will virtually completely phase separate from the amine solution without constant agitation, therefore necessitating this aggressive mixing process in order to ensure the reaction efficiency being achieved.) After the reaction is completed, the mixture is allowed to settle which results in the virtually complete separation of the amine phase (containing DIPA, water, and other components of the amine-containing solution but substantially free of HPOZD) from the caustic phase. After an appropriate settling interval, approximately ½ of the caustic phase is drawn off the bottom of the reaction mixture and placed in a "waste/neutralization tank." The remaining portion of the caustic phase and a very small portion of the amine phase are drawn off to a "recycle tank" for use in a subsequent reaction cycle or sent to the waste tank. The majority of the amine phase is passed through a heat exchanger and then treated in ion exchange resin beds. The resin beds use cation exchange resins to remove excess cations from the amine and cleaned amine is returned to the amine system.

A major difference between the present invention and the prior art is that the caustic phase is separated from the amine phase prior to passing the amine solution through the ion exchange resins. This separation is possible because a much higher caustic concentration is being used than was used in the prior art technique. This higher caustic concentration drives the conversion reaction to a higher conversion efficiency, typically converting 95% to 100% of the HPOZD to DIPA, necessitating less reprocessing of the amine-containing solution to eliminate HPOZD. An additional benefit of this change is that the amine phase contains only a small portion of the cations introduced into the reaction mixture (thus the caustic phase contains the majority of the cations introduced into the reaction mixture), therefore consuming much less ion exchange capacity per processed amine volume. This results in less rinse water returned to the amine system, less regeneration acid consumption by the resin beds and less waste per processed amine volume. Another side benefit of this present invention is that carbonates and/or bicarbonates are concentrated in the caustic phase which means that the majority of those species are not returned to the amine system. When neutralization of the caustic phase is performed, these carbonates and/or bicarbonates are reacted with the neutralizing acid and $CO_2$ is evolved from this neutralization process which is vented harmlessly to the atmosphere.

BRIEF DESCRIPTION OF THE SEVERAL VIEWS OF THE DRAWING

Other object features and advantages of the present invention will become apparent from the following detailed description taken in conjunction with the drawings in which.

DETAILED DESCRIPTION OF THE INVENTION

Figure 1:
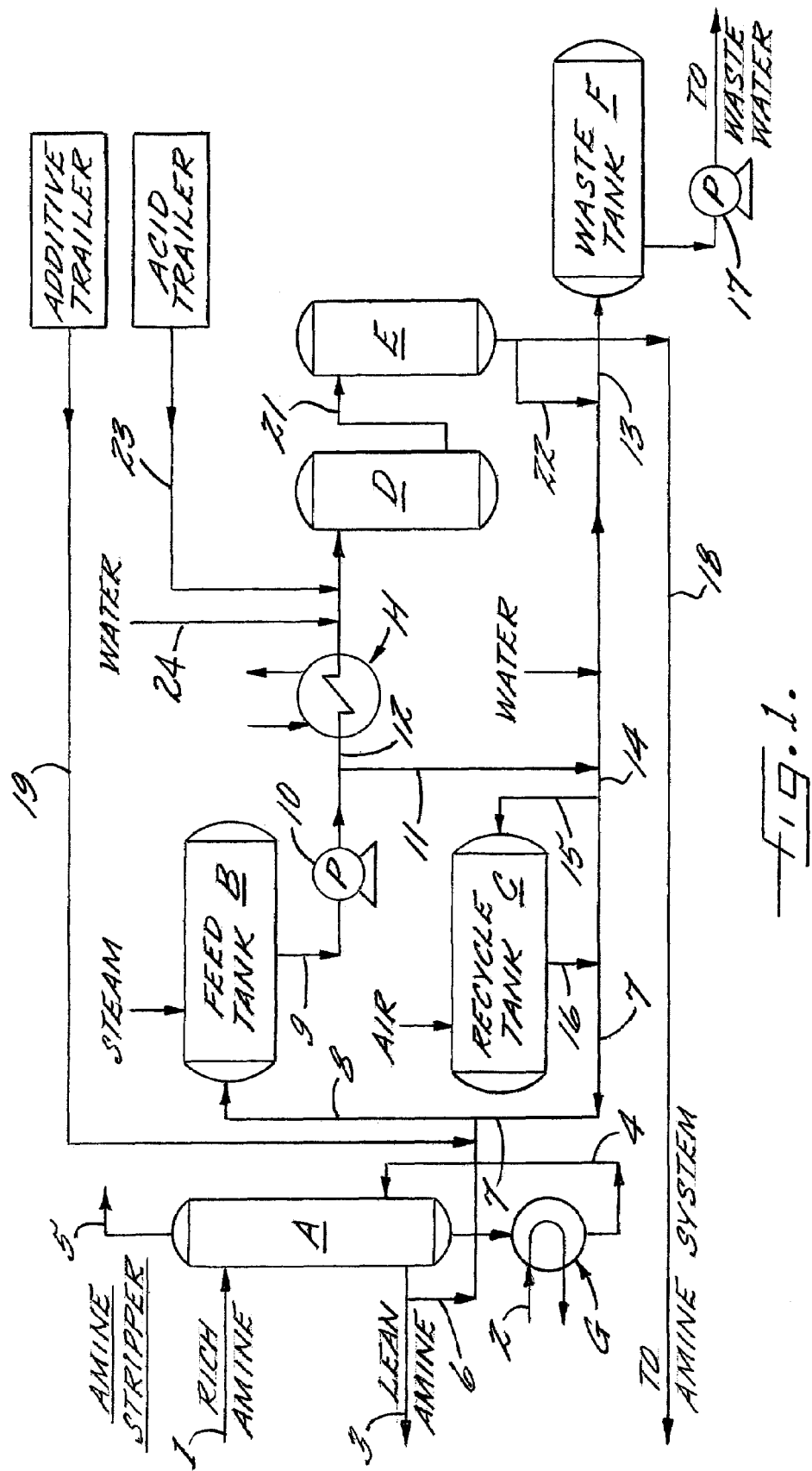
FIG. 1 is a schematic flow diagram which illustrates an embodiment of the present invention.

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Referring to FIG. 1, there is shown a schematic diagram of a regeneration process for converting hydroxypropyloxazolidone (HPOZD) molecule to di-isopropanolamine (DIPA) and $CO_2$. A rich amine stream (an amine containing considerable acid gasses entrained) from an absorber (not shown) is introduced to amine regenerator stripper column A through line 1. Internal stripping steam is generated by reboiling the amine solution in the stripper boiler (heat exchanger G) with a suitable heat medium 2. The lean amine (amine with minimal acid gasses entrained) stream 3 containing HPOZD exits the stripper at a temperature from about 105° C. to about 138° C. depending upon the concentration of the amine and the pressure in the stripper. The steam generated from the stripper boiler G is introduced near the bottom of the amine stripper column A through line 4 and passes upward through the amine solution as a stripping vapor to sweep the acid gasses away from the amine solution and out of the top of the stripper A. The mixture of steam, hydrogen sulfide, and carbon dioxide exits the stripper overhead through line 5.

The hot lean amine stream exits the bottom of amine stripper A and a major portion of it passes through line 3 back to the amine absorber (not shown). The remaining lean amine containing the HPOZD impurity passes through line 6 where it may be blended with a caustic solution either from a concentrated caustic supply (additive trailer, line 19) and/or from a "recycle caustic tank" (recycle tank C, line 16) which is then fed into the reaction tank (feed tank B) through line 8 for subsequent processing according to this invention where the caustic reacts with HPOZD to convert it to DIPA and $CO_2$.

The conversion of HPOZD to DIPA and $CO_2$ stoichiometrically requires two moles of hydroxide ($OH^-$) for each mole of HPOZD present in the solution to ensure a reasonably complete conversion of the HPOZD. However, it has been found that using that exact ratio does not provide sufficient driving force to cause the reaction to go to completion. Achieving complete conversion of the HPOZD back to DIPA requires a ratio of at least 2 but preferably more than 2.2 moles of hydroxide for each mole of HPOZD in the solution and one mole of hydroxide for each mole of "bound amine" (a protonated amine=an $H_+$ bound to the amine) present in the solution. More specifically, to have some residual recoverable caustic value in the caustic phase of the reaction mixture, a ratio of 2.5 moles of hydroxide for each mole of HPOZD present and at least one mole of hydroxide for each mole of "bound amine" present in the solution is desirable. (Note: A hydroxide molecule reacts with a bound amine molecule to free the amine molecule and yield one $H_2O$ molecule.)

The reaction is carried out in feed tank B at a temperature above 60° C., preferably between 60° C. and 120° C., and most preferably from 80° C. to 100° C. The reaction mixture is held in feed tank B at the reaction temperature while being constantly mixed so as to maximize the contact between the caustic phase and the lean amine solution, preferably for about 2 hours.

After the reaction is completed, the mixture is allowed to settle which results in the virtually compete separation of the amine solution (containing DIPA, water, and other components of the amine-containing solution but substantially free of HPOZD) from the caustic phase. After an appropriate settling interval, a portion (preferably approximately ½) of the caustic phase is drawn off the bottom of the reaction mixture and is pumped by pump 10 through lines 9, 11, 14, and 13 to the waste tank F for use later in neutralization of acids processed through cation exchange resins or to be neutralized by acid from the acid trailer (through a pump and a line not shown) to create a bio-remedial, non-hazardous waste stream that can be pumped through pump 17 to a waste treatment plant as a potassium sulfate and/or potassium carbonate and/or potassium bicarbonate salt solution. The remaining portion of the caustic phase and a very small portion of the amine phase are pumped by pump 10 through lines 9, 11, 14, and 15 to the recycle tank C where it can be used for subsequent reaction steps or it can be pumped through lines 16, 14, and 13 to the waste tank F. The majority of the amine phase is pumped by pump 10 through lines 9 and 12, through the heat exchanger H to cool the mixture, then through the cation exchange resin vessels D and E which use cation exchange resins (that may be the same or different) to remove the majority of the cations from the "clean amine" solution. This clean amine solution is subsequently returned through line 18 to the amine system for further use.

Suitable cation exchange resins include for example strong acid cation resins in the $H^+$ form such as Purolite C100, C145, SGC100, Sybron Ionac® C-251, CFP-110, Miles Wofatit KPS, Miles Lewatit S-100, Dowex® HCR-S/W2, Rohm & Haas Duolite C20/225, Resin Tech CG8, CG10 and the like.

Prior to regenerating the resins, the amine containing solution is rinsed off of the resin beds with water from line 24 and sent to the amine system. Any amine occupying resin exchange sites may also be removed by a caustic stripping process as described in U.S. Pat. No. 5,368,818 by drawing caustic from the additive trailer or some other source.

The cation exchange resins are regenerated by drawing acid from the acid trailer through line 23, blending with water from line 24 as needed, using a pump (not shown in FIG. 1), pumping the acid solution through line 12 to the resin beds to exchange the $K^+$ cations on the resin for $H^+$ cations. The exchanged $K^+$ cations are now in a salt solution which is passed through line 22 and 13 to waste tank F. After the regeneration process is completed, the resin beds are rinsed with water from line 24 through resin beds D and E to waste tank F via lines 22 and 13.

This entire processing cycle may be repeated multiple times, and for subsequent processing cycles, the material in recycle tank C is transferred back into feed tank B through use of a pump (not shown in FIG. 1) where it is combined with additional lean amine solution laden with HPOZD from the amine stripper and additional fresh caustic via line 19 from the additive trailer. By knowing the HPOZD content and the bound amine content of the amine solution added to the feed tank, the hydroxide requirement to achieve complete conversion of the HPOZD can be determined.

It should be understood that the amine regenerator (amine stripper column A) may be sized to regenerate amines from one to as many as 20 or so absorbers. The lean amine stream 3 would be used in all absorbers. The amine-containing solution may come from the exit of the stripper as shown in FIG. 1 or it may come from the reboiler circuit or any point in the lean amine circulation system or a storage vessel where a contaminated amine containing solution has been collected for processing.

EXAMPLES 1-3

These three examples illustrate actual laboratory experimentation on samples from three different locations with the intention of implementing the current invention's technology to perform the amine reclamation. Prior to testing, each amine solution was analyzed for % oxazolidone by gas chromatography, density, and % bound amine and % DIPA by acid/base titration.

The following parameters are conditions under which these experiments were performed for each sample individually:

An aliquot of the sample was selected and computations were made to determine the amounts of these listed species in that aliquot. This aliquot was placed into a 500-mL three necked boiling flask. A calculation was made to compute what amount of hydroxide (in the form of a 50% by weight potassium hydroxide solution) would be needed to present a ratio of 2.5 to 1 of hydroxide ions to reactable species. The amount of potassium hydroxide thus computed was added to the aliquot of amine in the boiling flask. A magnetic stirring bar was added to the flask, then the flask was placed in a hot water bath on top of a hot-plate stirring motor. A cold water condenser was placed into the center neck of the flask and a thermometer placed into one of the side necks of the flask. The third neck of the flask was capped with a stopcock. The flask's contents were vigorously stirred to completely mix the amine and caustic phases.

The flask and the water bath were heated to approximately 80° C. (plus or minus 3° C.) and held at that temperature for approximately two hours while the solution was continuously stirred to ensure complete mixing contact of the amine and caustic phases.

After the two hour mixing period was completed, the flask was removed from the heating and condensing apparatus and the solution was poured from the flask into a 500-mL separatory funnel. The phases were allowed to completely separate in the funnel and the bottom (caustic) phase was drawn off from the solution and segregated for subsequent analysis.

The reaction product amine phase was analyzed for residual oxazolidone by gas chromatography, DIPA by acid/base titration, residual strong cations (as potassium) and excess hydroxide by acid/base titration.

The reaction product caustic phase was analyzed for residual free hydroxide, carbonates and bicarbonates by acid/base titration but that information is not reported herein. This free hydroxide computation is important for the use of this phase as part of the subsequent batch's hydroxide source material.

Tabulated results of the analysis of each amine phase are shown in Table 1.

TABLE 1

| Description/Sample ID | Example 1 | Example 2 | Example 3 |
|---|---|---|---|
| Sample Density, g/mL | 1.082 | 1.115 | 1.080 |
| % Oxazolidone starting conditions | 12.25 | 18.83 | 29.78 |
| Oxazolidone starting conditions, mole/kg | 0.657 | 0.951 | 1.604 |
| Oxazolidone starting conditions, mole/L | 0.711 | 1.060 | 1.732 |
| Bound Amine, starting conditions, mole/kg | 0.044 | 0.026 | 0.049 |
| Bound Amine, starting conditions, mol/L | 0.048 | 0.029 | 0.053 |
| Total constituents to react with KOH, mol/L | 0.759 | 1.089 | 1.785 |
| % DIPA in amine phase prior to reaction, w/w | 49.61 | 34.86 | 47.57 |
| DIPA in amine phase prior to reaction, mol/kg | 3.725 | 2.617 | 3.572 |
| DIPA in amine phase prior to reaction, mol/L | 4.030 | 2.919 | 3.857 |
| Hydroxide Dosage Ratio: Mole:mole ratio of $OH^-$ to reactable constituents | 2.5 | 2.5 | 2.5 |
| Reacted Product's amine phase density, g/mL | 1.082 | 1.110 | 1.067 |
| Reacted Product's amine phase, % Oxazolidone remaining, w/w | 0.200 | 0.590 | 0.190 |

TABLE 1-continued

| Description/Sample ID | Example 1 | Example 2 | Example 3 |
|---|---|---|---|
| Reacted Product's amine phase, Oxazolidone remaining, mole/kg | 0.013 | 0.037 | 0.012 |
| Reacted Product's amine phase, Oxazolidone remaining, mole/L | 0.014 | 0.041 | 0.013 |
| % DIPA in Reacted Product's amine phase, w/w | 57.61 | 50.60 | 69.05 |
| Reacted Product's amine phase, DIPA, mole/kg | 4.325 | 3.799 | 5.184 |
| Reacted Product's amine phase, DIPA, mole/L | 4.679 | 4.215 | 5.532 |
| % Destruction of Oxazolidone | 98.09 | 96.12 | 99.26 |
| Net increase in DIPA concentration, mole/L | 0.65 | 1.30 | 1.67 |
| Net absolute increase in DIPA concentration, % by wt | 8.00 | 15.74 | 21.48 |

The results show a significant decrease in oxazolidone and a corresponding increase in DIPA concentration.

COMPARISON OF PRIOR ART AND THE PRESENT INVENTION

Samples of contaminated amine from various locations were obtained to compare the reduction of oxazolidone concentration in their process streams using the prior art and the new invention. These next two examples (example 4 in table 2 and example 5 in table 3) illustrate the contrast between the prior art and the predicted results using the present invention. The sixth example (table 4) contrasts expectations per the prior art and the actual observations during the commercial scale trial of the present invention.

EXAMPLE 4

System Size: 49,100 gallons
Starting Oxazolidone level: 20.4%;
Targeted end value Oxazolidone level: 8.0%
Oxazolidone incursion rate: 1 lbmol/day

TABLE 2

| Description | Prior Art, Actual Values (Commercial Scale) | Current Invention, Predicted Values |
|---|---|---|
| Cycles to perform job to specified parameters | 56 | 17 |
| Days to perform job to specified parameters | 23 | 7 |
| Fresh 50% KOH required for reacting with oxazolidone to convert it to amine, gallons | 4,000 | 5,900 |
| Fresh 50% KOH required for neutralization of resin regenerant waste, gallons | 4,872 | 0 |
| Fresh 50% KOH for stripping amine off of resin prior to regeneration, gallons | 1,120 | 340 |
| Recycled KOH made available by process for neutralization of acid waste, gallons | 0 | 1,475 |
| Recycled KOH required for neutralization of resin regenerant waste, gallons | 0 | 1,037 |
| Fresh 50% KOH total usage, gallons | 9,992 | 6,240 |
| 50% KOH predicted in brine solution, gallons (what does not get neutralized by the regenerant waste) | 0 | 438 |
| 93% H$_2$SO$_4$ needed for regeneration of resin, gallons | 3,920 | 1,071 |
| 93% H$_2$SO$_4$ needed for neutralization of waste KOH stream, gallons | 0 | 169 |
| 93% H$_2$SO$_4$ total usage, gallons | 3,920 | 1,240 |
| Effluent brine generated by process, gallons | 295,000 | 94,000 |
| Water introduced to amine system, gallons | 47,264 | 14,348 |

The results show the predicted dramatic reduction in water usage, caustic usage, acid usage, effluent brine production, and reaction cycles, and processing time, when practicing the method of the present invention.

EXAMPLE 5

System Size: 73,600 gallons
Existing Oxazolidone level: 23 wt %;
Targeted end value Oxazolidone level: 8 wt %
Oxazolidone incursion rate: 3 lbmol/day

TABLE 3

| Description | Prior Art Actual Values (Commercial Scale) | Current Invention Predicted Values |
|---|---|---|
| Cycles to perform job to specified parameters | 52 | 35 |
| Days predicted to perform job to specified parameters | 28 | 12 |
| Fresh 50% KOH total usage, gallons | 24,700 | 15,700 |
| 93% H$_2$SO$_4$ total usage, gallons | 6,240 | 3,243 |
| Effluent brine generated by process, gallons | 509,824 | 269,863 |
| Water introduced to amine system, gallons | 295,008 | 64,125 |

The results show the predicted dramatic reduction in water usage, caustic usage, acid usage, effluent brine production, and reaction cycles, and processing time, when practicing the method of the present invention.

EXAMPLE 6

System Size: 13,200 gallons
Starting Oxazolidone level: 37 wt %;
Targeted end value Oxazolidone level: 4.4 wt %
Oxazolidone incursion rate: 0.8 lbmol/day

TABLE 4

| Description | Prior Art, Predicted Values | Current Invention, Actual Data (Commercial Scale) |
|---|---|---|
| Cycles to perform job to specified parameters | 66 | 17 |
| Days predicted to perform job to specified parameters | 27 | 11 |
| Fresh 50% KOH total usage, m$^3$ | 38 | 28 |
| 93% H$_2$SO$_4$ total, m$^3$ | 18 | 8 |
| Effluent brine generated by process, m$^3$ | 1,300 | 180 |
| Water introduced to amine system, m$^3$ | 280 | 72 |
| Water usage total, m$^3$ | 1,850 | 126 |

The results show the actual dramatic reduction in water usage, caustic usage, acid usage, effluent brine production, and reaction cycles, and processing time, when practicing the method of the present invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A process for recovering alkanolamines comprising:
reacting a solution containing an alkanolamine, water, carbon dioxide and hydroxypropyloxazolidone, with a caustic solution providing hydroxide ions in a ratio of at least 2.0 moles per mole of hydroxypropyloxazolidone at a temperature between about 60° C. and about 120° C. to hydrolyze/convert the hydroxypropyloxazolidone to di-isopropanolamine and carbonates and/or bicarbonates, producing a caustic phase containing carbonates and/or bicarbonates and an amine phase containing di-isopropanolamine.

2. The process according to claim 1 wherein at least a portion of said caustic phase of said reacting step is recycled and used in subsequent reaction steps as a source of some of the needed hydroxide.

3. The process according to claim 1 wherein said ratio of hydroxide ions to hydroxypropyloxazolidone is at least 2.2 moles of hydroxide for each mole of hydroxypropyloxazolidone.

4. The process according to claim 1 wherein said temperature is between about 80° C. and about 100° C.

5. The process according to claim 1 wherein said caustic solution is comprises potassium hydroxide.

6. The process according to claim 1 wherein said alkanolamine is a primary or secondary alkanolamine.

7. The process according to claim 1 wherein said solution containing an alkanolamine also contains tetramethylene sulfone.

8. The process according to claim 1 wherein said amine phase is further treated by passing said amine phase through at least one cation exchange resin bed.

9. A process for regenerating an alkanolamine solution from an amine recirculating system comprising:

reacting a solution containing an alkanolamine, water, carbon dioxide and hydroxypropyloxazolidone and possibly a physical solvent with a caustic solution providing hydroxide ions in a ratio of at least 2.2 moles of hydroxide ion for each mole of hydroxypropyloxazolidone at a temperature between about 80° C. and about 100° C. to hydrolyze/convert the hydroxypropyloxazolidone to di-isopropanolamine and carbonates and/or bicarbonates producing an amine phase containing di-isopropanolamine and a caustic phase containing carbonates and/or bicarbonates;

recycling at least a portion of said caustic phase for a subsequent reaction step;

passing said amine phase through at least one cation exchange resin bed cations; and recovering said amine.

10. The process according to claim 9 wherein said caustic solution is potassium hydroxide.

11. The process according to claim 1 wherein said alkanolamine is di-isopropanolamine.

12. The process according to claim 6 wherein said primary or secondary alkanolamine is monoethanolamine, diethanolamine, methyl monoethanolamine, or di-isopropanolamine.

* * * * *

UNITED STATES PATENT AND TRADEMARK OFFICE
CERTIFICATE OF CORRECTION

PATENT NO. : 7,323,600 B1 Page 1 of 1
APPLICATION NO. : 11/463182
DATED : January 29, 2008
INVENTOR(S) : Turoff et al.

It is certified that error appears in the above-identified patent and that said Letters Patent is hereby corrected as shown below:

Column 10,

Line 19, cancel "cations".

Signed and Sealed this

Tenth Day of June, 2008

JON W. DUDAS
*Director of the United States Patent and Trademark Office*